(12) United States Patent
Lane et al.

(10) Patent No.: US 8,091,568 B2
(45) Date of Patent: Jan. 10, 2012

(54) TEMPORAL PHOTO-BLEACHING OF COLORED LENS CARE SOLUTIONS AND USE THEREOF

(75) Inventors: Jennifer Dawn Lane, Stone Mountain, GA (US); Dawn A. Smith, Duluth, GA (US)

(73) Assignee: Novartis AG, Basel (CH)

( * ) Notice: Subject to any disclaimer, the term of this patent is extended or adjusted under 35 U.S.C. 154(b) by 239 days.

(21) Appl. No.: 12/310,190

(22) PCT Filed: Aug. 14, 2007

(86) PCT No.: PCT/US2007/017963
§ 371 (c)(1),
(2), (4) Date: Feb. 12, 2009

(87) PCT Pub. No.: WO2008/021349
PCT Pub. Date: Feb. 21, 2008

(65) Prior Publication Data
US 2009/0199878 A1    Aug. 13, 2009

Related U.S. Application Data

(60) Provisional application No. 60/838,065, filed on Aug. 16, 2006.

(51) Int. Cl.
*B08B 3/04* (2006.01)
(52) U.S. Cl. .......... 134/93; 134/94.1; 134/901; 422/292
(58) Field of Classification Search ................... 134/901; 422/301
See application file for complete search history.

(56) References Cited

U.S. PATENT DOCUMENTS

| | | | | |
|---|---|---|---|---|
| 4,031,209 A * | 6/1977 | Krezanoski | .................... | 424/672 |
| 4,312,833 A * | 1/1982 | Clough et al. | .................. | 422/30 |
| 5,389,369 A * | 2/1995 | Allen | ........................... | 424/94.4 |
| 5,630,884 A | 5/1997 | Huth | ............................... | 134/27 |
| 5,989,847 A * | 11/1999 | Park et al. | ....................... | 435/28 |
| 6,033,662 A * | 3/2000 | Allen | ........................... | 424/94.4 |
| 6,099,800 A | 8/2000 | Cheng | ............................ | 422/30 |
| 6,126,706 A * | 10/2000 | Matsumoto et al. | ............ | 134/34 |
| 6,232,281 B1 * | 5/2001 | Willey et al. | ................... | 510/310 |
| 6,258,591 B1 * | 7/2001 | Yoneda et al. | ................ | 435/264 |
| 6,287,518 B1 * | 9/2001 | Ignacio et al. | ................. | 422/86 |

(Continued)

FOREIGN PATENT DOCUMENTS

| | | | |
|---|---|---|---|
| EP | 0 976 409 | | 2/2000 |
| JP | 2002006274 A | | 1/2002 |
| JP | 2003075253 A | | 3/2003 |
| JP | 2005-211545 | * | 8/2005 |
| NL | 1023255 | | 10/2004 |

OTHER PUBLICATIONS

WIPO WO 93/00815 Jan. 1993.*
PCT International Search Report.
PCT Written Opinion of the International Searching Authority.

(Continued)

*Primary Examiner* — Frankie L Stinson
(74) *Attorney, Agent, or Firm* — Sheng-Hsin Hu; Jian Zhou

(57) ABSTRACT

The present invention provides a lens care kit for disinfecting and cleaning contact lenses. The lens care kit of the invention allows customers to visually identify when their lenses are disinfected, clean, and ready to wear. The invention is relied on color change, due to temporally photo-bleaching of a colored lens care solution, to indicate the readiness of disinfection and cleaning of contact lenses.

19 Claims, 1 Drawing Sheet

U.S. PATENT DOCUMENTS

| | | | |
|---|---|---|---|
| 6,420,455 B1 * | 7/2002 | Landgrebe et al. | 523/122 |
| 6,440,411 B2 | 8/2002 | Scherer et al. | 424/94.4 |
| 6,790,409 B1 * | 9/2004 | Nakamura et al. | 422/22 |
| 6,991,831 B2 * | 1/2006 | Klemm | 427/475 |
| 2003/0100101 A1 * | 5/2003 | Huth et al. | 435/264 |
| 2004/0038956 A1 | 2/2004 | Nakada et al. | 514/191 |

OTHER PUBLICATIONS

English Translation of Japan Office Action Notification of Reasons For Rejection, Dispatch No. 405835, Dispatch Date: Jun. 21, 2011, Japanese Patent Application No. 2009-524661.

* cited by examiner

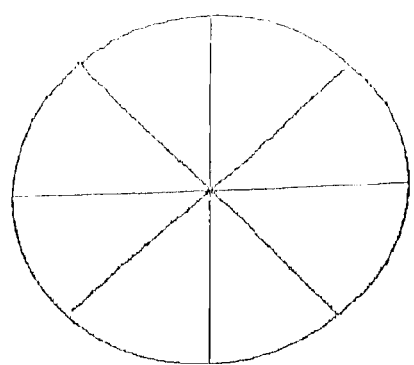
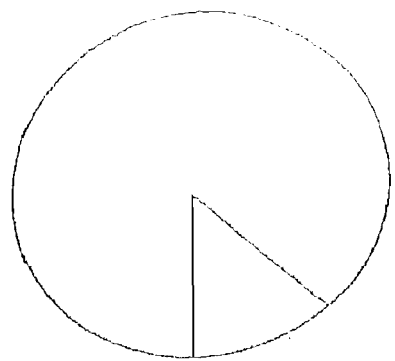
Fig. 1
Fig. 2
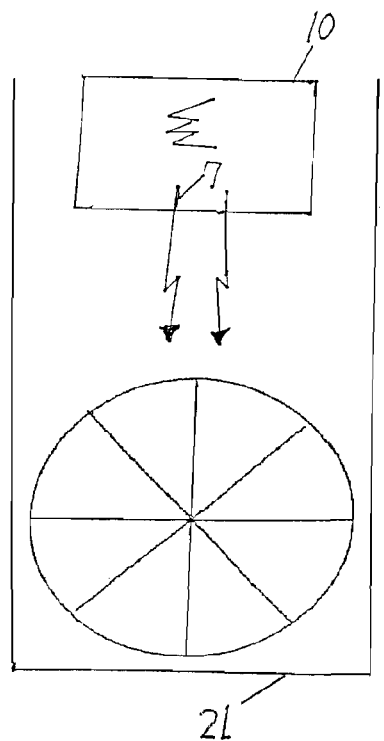
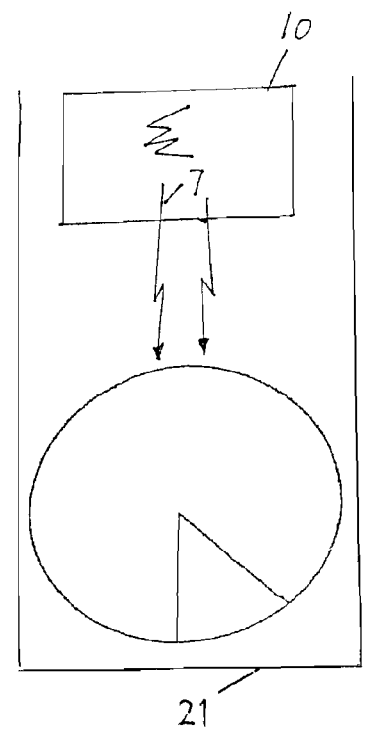
FIG. 3
FIG. 4

TEMPORAL PHOTO-BLEACHING OF COLORED LENS CARE SOLUTIONS AND USE THEREOF

This application is a national stage filing under 35 U.S.C. 371 of International Application No. PCT/US2007/017963 filed Aug. 14, 2007, which claims benefits of U.S. provisional application No. 60/838,065 filed Aug. 16, 2006.

This invention relates generally to a method and kit useful for cleaning and disinfecting a contact lens. In particular, the invention provides a method for color-codification of disinfecting and cleaning of contact lenses and kits for performing a method of invention for disinfecting and cleaning contact lenses.

BACKGROUND OF THE INVENTION

It is well known that a system of different colors (i.e., a color code) is very useful for displaying information. Examples of color codes include, without limitation, utility color codes which are used for identifying existing underground utilities in construction areas with the intent of protecting them from damage during excavation; 25 pair color code for electrical wiring; electronic color codes for indicating the values or ratings of electronic components; etc. It is generally easy for people to associate a color with an information. However, color is barely used in contact lens care field to codify disinfecting and cleaning of a contact lens.

Contact lenses provide a means for vision correction for a wide range of consumers. The advantages of contact lens wear are numerous. Improved convenience and improved appearance in comparison to spectacle glasses are probably the two most important advantages to most consumers. However, contact lenses require stringent care regimes in order to ensure comfort and avoid ocular infections. Proper care of contact lenses typically requires the consumer to periodically clean and disinfect the lenses, to prevent infection or other deleterious effects on ocular health which may be associated with contact lens wear.

In recent years, multiple-purpose solutions, which clean, disinfect, and rinse contact lenses all without mechanically rubbing lenses, have been developed as a new type of lens care systems. These new systems start dominating the most of the lens care market. Such popularity is most likely derived from the easiness and convenience provided by these new systems to consumers. In order to achieve a satisfactorily disinfecting result, a contact lens has to be in a MPS solution for a sufficient time period. But, consumers do not have a direct way to determine if their lenses have been in the lens care solution long enough to disinfect the lenses.

Thus, it would be desirable to provide a color indicator the color of which changes over time to enable customers to visually identify when their lenses are clean and ready to wear. As such, there exists a need for a lens care kit capable of discoloring or changing color over the time period required for disinfection of contact lenses.

SUMMARY OF THE INVENTION

Generally described, the present invention provides a lens care kit for cleaning and disinfecting contact lenses, comprising a colored lens care solution including a water-soluble colorant; and a lens case, wherein the lens case includes a light radiation source for irradiating the colored lens care solution, gradually decomposing the colorant, and rendering the colored lens care solution colorless over a specific time period, thereby indicating that lenses under disinfecting and cleaning by the colored lens care solution are ready for use. The lens care kit of the invention allows customers to visually identify when their lenses are disinfected, clean, and ready to wear, by observing disappearing of a color, preferably blue.

The present invention provides the foregoing and other features, and the advantages of the invention will become further apparent from the following detailed description of the example embodiments set forth herein. The detailed description are merely illustrative of the invention and do not limit the scope of the invention, which is defined by the appended claims and equivalents thereof.

BRIEF DESCRIPTION OF DRAWINGS

FIG. 1 illustrates a solid support has a pinwheel configuration and can be fitted in the bottom of a lens case for treating a contact lens according to a preferred embodiment of the invention.

FIG. 2 illustrates the top view of the pinwheel shown in FIG. 1.

FIG. 3 illustrates an irradiating source with the pinwheel shown in FIG. 1; wherein a lens case 21 and radiation 7 from the light-radiation source 10.

FIG. 4 illustrates an irradiating source with the pinwheel shown in FIG. 2; wherein a lens case 21 and radiation 7 from the light-radiation source 10.

DETAILED DESCRIPTION OF PREFERRED EMBODIMENTS

Unless defined otherwise, all technical and scientific terms used herein have the same meaning as commonly understood by one of ordinary skill in the art to which this invention belongs. Generally, the nomenclature used herein is well known and commonly employed in the art. Conventional methods are used for carrying out the disclosed procedures, such as those provided in the art and various general references. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification including the appended claims, reference to singular forms such as "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

The invention, in one aspect, provides a lens care kit for cleaning and disinfecting contact lenses, comprising: a colored lens care solution including a water-soluble colorant; and a lens case, wherein the lens case includes a light radiation source for irradiating the colored lens care solution, gradually decomposing the colorant, and rendering the colored lens care solution colorless over a specific time period, thereby indicating that lenses under disinfecting and cleaning by the colored lens care solution are ready for use.

A lens care kit of the invention can be used to disinfect and clean contact lenses including hard (PMMA) contact lenses, soft (hydrophilic) contact lenses, and rigid gas permeable (RGP) contact lenses. The soft contact lenses are hydrogel contact lens or silicone hydrogel contact lenses.

A "hydrogel" refers to a polymeric material which can absorb at least 10 percent by weight of water when it is fully hydrated. Generally, a hydrogel material is obtained by polymerization or copolymerization of at least one hydrophilic monomer in the presence of or in the absence of additional monomers and/or macromers.

A "silicone hydrogel" refers to a hydrogel obtained by copolymerization of a polymerizable composition comprising at least one silicone-containing vinylic monomer or at least one silicone-containing macromer.

"Hydrophilic," as used herein, describes a material or portion thereof that will more readily associate with water than with lipids.

The lens care kit of the invention allows-customers to visually identify when their lenses are disinfected, clean, and ready to wear. The invention is relied on photo-bleaching of color bleach to indicate the readiness of disinfection and cleaning of contact lenses. Preferably, the initial color is blue or green or purple. It is understood that any other color can be used. In accordance with the invention, the lens care solution has a color that is gradually bleached over a controlled time period. Preferably, at the end of the controlled time period, the color of the lens care solution is substantially disappeared and becomes substantially clear (substantially colorless but transparent). The controlled time period is sufficient long for disinfecting contact lenses and is preferably at least about 2 hour, more preferably about 4 hours; even more preferably about 6 hours.

A colored lens care solution of the invention comprises a water-soluble colorant. In accordance with the invention, the colorant should be a non-toxic dye and does not foul or stain contact lenses and lens cases.

In a preferred embodiment, any dyes, which can be degraded (bleached) by UV or visible light within a controlled specific time period, can be used in the invention. Examples of such dyes include, without limitation; vinylsulfones, reactive azo dyes, coumarin based dyes. Preferred colorants used in this preferred embodiment are thionin dyes; algae extract, e.g., LinaBlue AE, LinaBlue HGE, LinaBlue A, LinaBlue HK, Lineablue HG, all of which are marketed by Dainippon Ink & Chemicals Inc., Japan; purified allophycocyanin and phycocyanin from Sigma. Thionin dyes can be modified by attaching a polyethylene glycol polymeric tail to them in order to prevent the dyes from being absorbed by lens material based on size alone and to decrease their toxicity. A person skilled in the art will know how to covalently attach a polymer onto a dye.

In another preferred embodiment, a colored lens care solution containing a colorant is used in couple with a singlet oxygen generating agent.

Examples of dyes, which can be used in this preferred embodiment, include, without limitation, coomassie blue, EvoBlue30, malachite green, Victoria blue, remazol brilliant blue, acid blue 62, sanoline green, LinaBlue AE, luminal, lumigen, bromophenol blue, methylene blue, bromocresol blue, thymol blue, methyl crystal purple, tetraphenylporphyrin, triphenylamine dyes—brilliant green, triphenylamine dyes—crystal violet, benzoyl anthraquinone, dibezanthron dye (celadon jade green), indanthrene blue, brilliant cresyl blue, 2,6 dichlorophenolindophenol Na Salt, N,N dimethyl-1,4-phenylene diammonium dichloride, diphenylamine, toluidine blue, diphenyl benzidine, safranin, thionine, variamine blue salt B, alizarin, isatin; kermesic acid, FD&C Blue #1, FD&C Blue #2, FD&C green #3, D&C Blue #4; D&C green #5, Ex D&C violet #2, D&C green #8, D&C violet #2, Sandolan blue E HRC, Handolan Milling blue NVC, Dimarine blue K35L, dimarine brilliant blue K-BL, cartasol blue GDF, Cartasol brilliant violent SBF, diphenylamine, diphenylbenzidine, and sprillium blue. Preferred dyes are FD&C Blue No 1, Sanoline Blue, and Remazol Blue. Most preferred dye is FD&C Blue No 1.

In accordance with the invention, one or more colorants can be used together in the colored lens care solution to create desired color. A person skilled in the art will knows well how to select types of colorants and amounts thereof to achieve a desired color.

Singlet oxygen is a highly reactive species which can react with the double bonds in a dye molecule.

In accordance with the invention, a singlet oxygen-generating agent is intended to describe a compound capable of generating singlet oxygen under UV/visible light irradiation. Exemplary preferred singlet oxygen-generating compounds include without limitation Rose Bengal, methylene blue, Azure A, various zinc porphyrins (e.g., zinc tetrahydrophenyl-porphyrin, zinc tetracarboxyphenylporphyrin, zinc uroporphyrin, zinc protoporphyrin, or the like). Rose Bengal, methylene blue, and Azure A are most preferred singlet oxygen-generating compounds, because of their inertness to singlet oxygen.

In accordance with the invention, a singlet oxygen-generating agent is covalently attached to the solution-contacting surface of a lens case for treating contact lenses, or to the surface of a solid support, such as glasses, resins, or cloth tissues. A layer of a singlet oxygen-generating agent can be attached covalently onto a solid support or lens case by optionally first functionalizing the surface of the solid support or lens case (if there is no functional groups on the surface) to, obtain function groups and then covalently attaching the layer of singlet oxygen-generating agent. Surface modification (or functionalization) of a solid support is well known to a person skilled in the art. Any known suitable method can be used.

Singlet oxygen agents can be bound covalently to the functionalized surface of a solid support or directly onto the functional groups on the surface of the solid support or directly onto the surface of a lens case. This may be either a direct reaction or, preferably, a reaction in which a coupling agent is used. For example, one or more amine groups may be reacted directly with isothiocyanate, acyl azide, N-hydroxysuccinimide ester, sulfonyl chloride, an aldehyde, glyoxal epoxide, carbonate, aryl halide, imido ester, or anhydride groups.

Alternatively, coupling agents may be used. Coupling agents useful for coupling singlet oxygen-generating agent to the surface of a solid support include, without limitation, N.N'-carbonyldiimidazole, carbodiimides such as 1-ethyl-3-(3-dimethylaminopropyl)carbodiimide ("EDC"), dicyclohexyl carbodiimide, 1-cyclohexyl-3-(2-morpholinoethyl)carbodiimide, diisopropyl carbodiimide, or mixtures thereof. The carbodiimides also may be used with N-hydroxysuccinimide or N-hydroxysulfosuccinimide to form esters that can react with, amines to form amides.

Amino groups also may be coupled to the surface of a solid support by the formation of Schiff bases that can be reduced with agents such as sodium cyanoborohydride and the like to form hydrolytically stable amine links. Coupling agents useful for this purpose include, without limitation, N-hydroxysuccinimide esters, such as dithiobis(succinimidylpropionate), 3,3'-dithiobis(sulfosuccinimidylpropionate), disuccinimidyl suberate, bis(sulfosuccinimidyl)suberate, disuccinimidyl tartarate and the like, imidoesters, including, without limitation, dimethyl adipimate, difluorobenzene derivatives, including without limitation 1,5-difluoro-2,4 dinitrobenzene, bromofunctional aldehydes, including without limitation gluteraldehyde, and his epoxies, including without limitation 1,4-butanediol diglycidyl ether. One ordinarily skilled in the art will recognize that any number of other coupling agents may be used depending on the functional groups present on the surface of a solid support.

A lens case typically comprises a main body portion which includes a pair of separate and discrete wells (cavities or reservoirs) each adapted to receive one contact lens and an amount of a lens care solution. Each well has an open end having a substantially circular, oval or rain-drop shape periphery defining an opening. The lens case further comprises one or two caps adapted to be affixed to the wells at their open ends so as to provide a substantially liquid-impermeable seal. The caps each further include a sealing rim or surface adapted to mate with peripheries surrounding wells. The lens case may be constructed of a material which is sturdy and impervious to chemicals contained in a lens solution. For example, polystyrene, high-density polyethylene, or polypropylene can be the construction material of choice, although others may be used.

Preferably, singlet oxygen-generating agent attached to a solid support can be placed in a lens case's compartment in fluid communication with the well of a lens case for holding a contact lens and a given amount of a lens care solution.

Even more preferably, a solid support has a pinwheel configuration within the confines of a lens case, as disclosed in a co-pending U.S. patent application Ser. No. 12/309,347, entitle "Lens Care Methods and Kits", herein incorporated by reference in its entirety. This pinwheel configuration is covered with a top that allows only a small piece of the pinwheel to be exposed to the lens care solution and light irradiation. After a number of uses (i.e., disinfection of a contact lens), the top of the pinwheel is rotated to allow a fresh amount of singlet oxygen-generating agent to be exposed to the lens care solution and to light irradiation, and as such, the colorant can be decomposed by the singlet oxygen generated by the fresh singlet oxygen-generating agent under light irradiation.

In a further preferred embodiment, a colored lens care solution containing a colorant is used in couple with a semiconductor-based photocatalyst.

Semiconductor-based photocatalysts have been demonstrated to be able to photo decompose organic materials in solutions. Examples of semiconductor-based photocatalysts include without limitation $TiO_2$, SnO, CdS. The most preferred photocatalyst is $TiO_2$ because of its stability, photocatalytic efficiency; environmental friendliness, availability, and low cost. The degradation mechanism using a semiconductor-based photocatalyst, e.g., $TiO_2$, is generally When photocatalyst titanium dioxide (TiO2) absorbs Ultraviolet (UV) radiation (wavelength $\lambda < 388$ nm) from sunlight or illuminated light source (fluorescent lamps), an electron is excited from the valence band to the conduction band of $TiO_2$, producing a positive charge (hole, $h^+$) and a negative charge (electron, $e^-$). This stage is referred as the semiconductor's photo-excitation state. The energy difference between the valence band and the conduction band is known as the band gap. Wavelength of the light necessary for photo-excitation for a given semiconductor depends upon its band gap. The positive-hole of titanium dioxide oxidizes an electron donor (e.g., break apart the water molecule to form hydrogen gas and hydroxyl radical), and the electron of titanium dioxide reduces an electron acceptor (e.g., react with oxygen molecule to form super oxide anion). This cycle continues when light is available. The hydroxyl radical and super oxide anion can further react with a colorant to decompose it, thereby bleaching (discolorizing) a colored lens care solution.

Titanium dioxide can be applied directly onto the solution-contacting surface of a lens case or onto the surface of a solid support to form a coating thereon. Various embodiments of solid supports described above can be used in this embodiment.

One advantage of using a singlet oxygen-generating agent or a semiconductor-based photocatalyst in the invention is that bactericidal agents, singlet oxygen, hydroxyl radical and super oxygen anion, which are generated under light irradiation, can kill bacteria present in the solution derived from the worn lenses.

In accordance with the invention, a light radiation source can be any light sources known to a person skilled in the art, so long as the light source can emit a light which can photobleach a colorant in a colored lens care solution, can excite a singlet oxygen-generating agent to generate singlet oxygen, or can excite a semiconductor-based photocatalyst to its photo-excitation state (pairs of hole and electron). Preferred light source is light emitting device (LED). A LED would turn on inside the lens case after the lens case caps for the lens case are placed into place in a sealed state. A person skilled in the art will know well how to select a LED for a given colorant, singlet oxygen-generating agent, or semiconductor-based photocatalyst.

In preferred embodiments, a time delay switch could be added to the LED which would allow the LED to turn on only after a set time if the reaction occurred too quickly after the onset of the light induced reactions.

In accordance with the invention, a colored lens care-solution is ophthalmic safe. The term "ophthalmically safe" with respect to a lens care solution is meant that a contact lens treated with the solution is safe for direct placement on the eye without rinsing, that is; the solution is safe and sufficiently comfortable for daily contact with the eye via a contact lens. An ophthalmically safe solution has a tonicity and pH that is compatible with the eye and comprises materials, and amounts thereof, that are non-cytotoxic according to international ISO standards and U.S. FDA regulations.

The term "compatible with the eye" means a solution that may be in intimate contact with the eye for an extended period of time without significantly damaging the eye and without significant user discomfort.

A colored lens care solution can be a prepared from any lens care solutions including commercially available lens care solutions by adding one or more colorants therein. A lens care solution can be a multiple purpose solution (free of hydrogen peroxide) or a hydrogen peroxide containing solution.

Where a lens care solution is a hydrogen peroxide containing solution, the colored lens care solution is preferably prepared immediately prior to lens disinfection in a lens case by mixing two solutions, one hydrogen peroxide containing solution free of colorant and the other solution containing colorant and free of hydrogen peroxide. Such mixing can be achieved used a container having two separate compartments, one for hydrogen peroxide containing solution and the other for the colorant containing solution free of hydrogen peroxide. The container can further comprise a mixing mechanism known to a person skilled in the art to mix the two solutions when pouring out the two solutions from the container. By separately storing a hydrogen peroxide containing solution and a colorant containing solution and mixing them on-demand to form a colored lens care (disinfecting) solution, one may minimize or eliminate the possibility of the colorant being oxidize slowly by hydrogen peroxide and thereby greatly increases the shelf lifetimes of the solutions.

In accordance with the invention, a hydrogen-peroxide containing solution can further comprises other components known to a person skilled in the art, for example, tonicity agent (e.g., sodium chloride, potassium chloride, mannitol, xylitol, dexpenthanol, dextrose, glycerin, propylene glycol, and mixture thereof), conditioning/wetting agents (polyvinyl alcohol, polyoxamers, polyvinyl pyrrolidone, hydroxypropyl cellulose, and mixture thereof buffering agents, surfactants, and the like.

Where a lens care solution is a hydrogen-peroxide-free disinfecting solution, such as, for example, a multiple purpose solution; a colorant can be directly added into it to prepare a colored lens care solution of the invention, because of the absence of hydrogen peroxide.

In a preferred embodiment, the lens care solution of the invention is a multipurpose solution capable of disinfecting, cleaning, and rinsing a contact lens.

The term "disinfecting solution" means a solution containing one or more microbiocidal compounds, that is effective for reducing or substantially eliminating the presence of an array of microorganisms present on a contact lens, which can be tested by challenging a solution or a contact lens after immersion in the solution with specified inoculums of such microorganisms.

A solution that is useful for cleaning, chemical disinfection, storing, and rinsing an article, such as a contact lens, is referred to herein as a "multi-purpose solution." Such solutions may be part of a "multi-purpose solution system" or "multi-purpose solution package." The procedure for using a multi-purpose solution, system or package is referred to as a "multi-functional disinfection regimen." Multi-purpose solutions do not exclude the possibility that some wearers, for example, wearers particularly sensitive to chemical disinfectants or other chemical agents, may prefer to rinse or wet a contact lens with a another solution, for example, a sterile saline solution prior to insertion of the lens. The term "multi-purpose solution" also does not exclude the possibility of periodic cleaners not used on a daily basis or supplemental cleaners for removing proteins, for example enzyme cleaners, which are typically used on a weekly basis.

A colored hydrogen-peroxide-free disinfecting solution of the invention can be used to disinfect contact lenses against a wide range of microorganisms including but not limited to *Fusarium solani, Staphylococcus aureus, Pseudomonas aeruginosa, Serratia marcescens* and *Candida albicans*. For the purposes of the present invention the term "disinfect" means the rendering non-viable of substantially all pathogenic microbes that are in the vegetative state, including gram negative and gram positive bacteria, as well as fungi. The chemical compounds and compositions that render such pathogenic microbes inactive are known as microbicides.

A colored disinfecting or MPS solution of the invention must contain a microbicide in a concentration sufficient to effect the desired disinfection of a contact lens. The specific concentrations required for the microbicides useful in this invention must be determined empirically for each microbicide. Some of the factors affecting the effective concentration are specific activity of the microbicide against the specified pathogens, the molecular weight of the microbicide, and the solubility of the microbicide. It is also important that the chosen microbicides be employed in a physiologically tolerable concentration. The list of microbicides which may be employed in the present invention include, but is not in limited to biguanides, biguanide polymers, salts thereof, N-alkyl-2-pyrrolidone, polyquarternium-1 bronopol, benzalkonium chloride, and hydrogen peroxide. The presently useful antimicrobial biguanides include biguanides, biguanide polymers, salts thereof, and mixtures thereof. Preferably, the biguanide is selected from alexidine free-base, salts of alexidine, chlorhexidine free-base, salts of chlorhexidine, hexetidine, hexamethylene biguanides, and their polymers, and salts thereof. Most preferably, the biguanide is a hexamethylene biguanide polymer (PHMB), also referred to as polyaminopropyl biguanide (PAPB).

Typical solutions of this invention contain the microbicides PHMB in an amount of from about 0.01 to about 10 ppm, preferably from about 0.05 to about 5 ppm, more preferably from about 0.1 to about 2 ppm, even more preferably from about 0.2 to about 1.5 pp.

Although PHMB has a broad spectrum of activity and non-specific mode of action against bacteria, PHMB might be able to cause some level of corneal staining (Lyndon Jones, et. al. "Asymptomatic corneal staining associated with the use of balafilcon silicon-hydrogel contact lenses disinfected with a polyaminopropyl biguanide—preserved care regimen", Optometry and Vision Science 79: 753-61 (2002)). Therefore, it would be desirable to lower the amount of PHMB in a lens care solution while maintaining the antimicrobial efficacy of the lens care solution.

The present solutions preferably include an effective amount of a chelating component. Any suitable, preferably ophthalmically acceptable, chelating component may be included in the present compositions, although ethylenediaminetetraacetic acid (EDTA), salts thereof and mixtures thereof are particularly effective. EDTA is low level non-irritating chelating agent and can be synergistic with PHMB to increase antimicrobial efficacy. Typical amount of EDTA is from about 0.001% to about 1% by weight, preferably from about 0.002% to about 0.5% by weight, more preferably from about 0.004% to about 0.1, even more preferably from about 0.005 to about 0.05, based on the total amount of contact lens care composition.

The solution of the present invention preferably contains a buffering agent. The buffering agents maintain the pH preferably in the desired range, for example, in a physiologically acceptable range of about 6.0 to about 8.0. Any known, physiologically compatible buffering agents can be used. Suitable buffering agents as a constituent of the contact lens care composition according to the invention are known to the person skilled in the art. Examples are boric acid, borates, e.g. sodium borate, citric acid, citrates, e.g. potassium citrate, bicarbonates, e.g. sodium bicarbonate, TRIS (trometamol, 2-amino-2-hydroxymethyl-1,3-propanediol), bis-aminopolyols, phosphate buffers, e.g. $Na_2HPO_4$, $NaH_2PO_4$, and $KH_2PO_4$ or mixtures thereof. The amount of each buffer agent is that amount necessary to be effective in achieving a pH of the composition of from about 6.5 to about 7.5. Typically, it is present in an amount of from 0.001% to 2%, preferably from 0.01% to 1%; most preferably from about 0.05% to about 0.30% by weight.

The preferred buffering agents are bis-aminopolyols of formula (I)

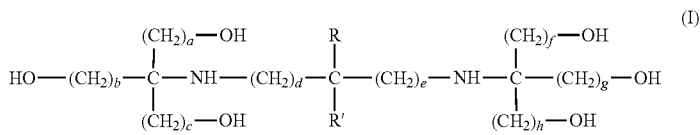

wherein a, b, c, d, e, f, g, and h are independently an integer from 1 to 6; and R and R' are independently selected from the group consisting of —H, —CH$_3$, —(CH$_2$)$_{2-6}$—H, and —(CH$_2$)$_{1-6}$—OH. In the present invention, the buffering agents described by formula (I) may be provided in the form of various water-soluble salts. A most preferred bis-aminopolyol is 1,3-bis(tris(hydroxymethyl)methylamino)propane (bis-TRIS-propane).

It has been found that bis-TRIS-propane can exhibit a synergy with certain, microbicides (e.g., PHMB) and fungicides, resulting in a microcidal activity significantly higher than the activity of these same active ingredients used in conjunction with other buffers. BIS-TRIS propane is described under biological buffers in Biochemicals and Reagents, Sigma-Aldrich Co., 2000-2001 edition. The specific structure of bis-TRIS-propane is shown in formula II.

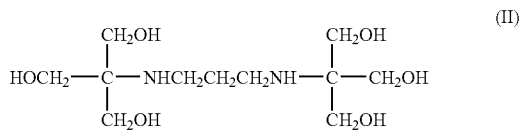

The dissociation constants for this dibasic compound are pKa$_1$=6.8 and pKa$_2$=9.5 which renders aqueous solutions of this compound useful as a buffering agent in a broad pH range from about 6.3 to 9.3. bis-TRIS-propane at a concentrations used in this invention is harmless to the eye and to known contact lens materials and is, therefore, ophthalmically compatible:

A colored lens care solution of the invention preferably comprises a lubricant. "Lubricants" as used herein refer to any compounds or materials which can enhance surface wettability of a contact lens and/or the eye or reduce the frictional character of the contact lens surface. Examples of lubricants include without limitation mucin-like materials and hydrophilic polymers.

Exemplary mucin-like materials include without limitation polyglycolic acid, polylactides, collagen, and gelatin. A mucin-like material may be used to alleviate dry eye syndrome. The mucin-like material preferably is present in effective amounts.

Exemplary hydrophilic polymers include, but are not limited to, polyvinylalcohols (PVAs), polyamides, polyimides, polylactone, a homopolymer of a vinyl lactam, a copolymer of at least one vinyl lactam in the presence or in the absence of one or more hydrophilic vinylic comonomers, a homopolymer of acrylamide or methacrylamide, a copolymer of acrylamide or methacrylamide with one or more hydrophilic vinylic monomers, mixtures thereof.

The solution may also contain one or more viscosity-enhancing agents. Suitable viscosity-enhancing components include, but are not limited to, polyvinylpyrrolidone, water soluble natural gums, cellulose-derived polymers, and the like. Useful natural gums include guar gum, gum tragacanth and the like. Examples of useful cellulose-derived polymers as viscosity-enhancing agents include without limitation cellulose ethers.

Exemplary preferred cellulose ethers are methyl cellulose (MC), ethyl cellulose, hydroxymethylcellulose, hydroxyethyl cellulose (HEC), hydroxypropylcellulose, hydroxypropylmethyl cellulose (HPMC), or a mixture thereof. More preferably, a cellulose ether is hydroxyethyl cellulose (HEC), hydroxypropylmethyl cellulose (HPMC), and mixtures thereof. The cellulose ether is present in the composition in an amount of from about 0.01% to about 5% by weight, preferably from about 0.05% to about 3% by weight, even more preferably from about 0.1% to about 1% by weight, based on the total amount of contact lens care composition. It is believed that a cellulose ether can be used to increase the viscosity of a lens care and also can serve as a lubricant in the lens care composition.

A very useful viscosity-enhancing component is polyvinylpyrrolidone (PVP). The polyvinylpyrrolidone (PVP) used in the compositions of the invention is a linear homopolymer or essentially a linear homopolymer comprising at least 90% repeat units derived from 1-vinyl-2-pyrrolidone monomers, the polymer more preferably comprising at least about 95% or essentially all of such repeat units, the remainder selected from polymerization-compatible monomers, preferably neutral monomers, such as alkenes or acrylates. Other synonyms for PVP include povidone, polyvidone, 1-vinyl-2-pyrrolidinone, and 1-ethenyl-2-pyrolionone (CAS registry number 9003-39-8). The PVP used in the present invention suitably has a weight average molecular weight of about 10,000 to 250,000, preferably 30,000 to 100,000. Such materials are sold by various companies, including ISP Technologies, Inc. under the trademark PLASDONE™ K-29/32, from BASF under the trademark KOLLIDON™ for USP grade PVP, for example KOLLIDON™ K-30 or K-90. While the invention is not limited to any specific PVP, K-90 PVP is preferred, more preferably pharmaceutical grade.

The colored lens care solutions according to the invention are preferably formulated in such a way that they are isotonic with the lachrymal fluid. A solution which is isotonic with the lachrymal fluid is generally understood to be a solution whose concentration corresponds to the concentration of a 0.9% sodium chloride solution (308 mOsm/kg). Deviations from this concentration are possible throughout, provided that the contact lenses to be treated are not damaged.

The isotonicity with the lachrymal fluid, or even another desired tonicity, may be adjusted by adding organic or inorganic substances which affect the tonicity. Suitable occularly acceptable tonicity agents include, but are not limited to sodium chloride, potassium chloride, glycerol, propylene glycol, polyols; dexpanthenol, mannitols, xylitol, sorbitol, and mixtures thereof. Preferably, the majority of the tonicity of the solution is provided by one or more compounds selected from the group consisting of non-halide containing electrolytes (e.g., sodium bicarbonate) and non-electrolytic compounds. The tonicity of the solution is typically adjusted to be in the range from about 200 to about 450 milliosmol (mOsm), preferably from about 250 to 350 mOsm.

In accordance with the invention the colored lens care solution can further comprise a surfactant for cleaning the contact lens. Any suitable known surfactants can be used in the invention. Examples of suitable surfactants include, but are not limited to poloxamers under the tradename Pluronic from BASF Corp. (Pluronic™ and Pluronic-R™) which are nonionic surfactants consisting of block copolymers of propylene oxide and ethylene oxide; poloxamine which is a block copolymer derivative of ethylene oxide and propylene oxide combined with ethylene diamine; tyloxapol, which is 4-(1,1,3,3-tetramethylbutyl)phenol polymer with formaldehyde and oxirane; ethoxylated alkyl phenols, such as various surface active agents available under the tradenames TRITON (Union Carbide, Tarrytown, N.Y., USA) and IGEPAL (Rhone-Poulenc, Cranbury, N.J., USA); polysorbates such as polysorbate 20, including the polysorbate surface active agents available under the tradename TWEEN (ICI Americas, Inc., Wilmington, Del., USA.); alkyl glucosides and polyglucosides such as products available under the tradename PLANTAREN (Henkel Corp., Hoboken, N.J., USA); and polyethoxylated castor oils commercially available from BASF under the trademark CREMAPHOR.

Preferred surfactants include homopolymers of polyethylene glycol or polyethyleneoxide; and certain poloxamers such as materials commercially available from BASF under the tradenames PLURONIC® 17R4, PLURONIC® F-68NF, PLURONIC® F68LF, and PLURONIC® F127, with PLURONIC® F-68NF (National Formulary grade) being the most preferred. More preferably, a combination of PLURONIC® 17R4 and PLURONIC® F127 is used. When present, poloxamers may be employed at from about 0.001% to about 5% by weight, preferably from about 0.005% to about 1% by weight, more preferably from about 0.05% to about 0.6% by weight.

The colored lens care solutions according to the invention are produced in known manner, in particular by means of conventional mixing of the constituents with water or dissolving the constituents in water.

The kit can optionally include instructions for how to use the lens care solution to clean and lubricate contact lenses directly in eyes.

The contact lens can be contacted with the solution by immersing the lens in a colored lens care solution of the invention in a lens case. Although not necessary, the solution containing the contact lens can be agitated, for example, by shaking the lens case containing the solution and contact lens, to at least facilitate removal of deposit material from the lens.

In another aspect, the invention provides a method for cleaning and/or disinfecting a contact lens. The method comprises the steps of: bringing one or more contact lenses into contact with a colored lens care solution including a colorant in a lens case a light radiation source for irradiating the colored lens care solution; irradiating the colored lens care solution for a specified time period; and observing change in the color of the colored lens care solution, substantially discoloring of the colored lens care solution indicating that the lenses under disinfecting and cleaning by the colored lens care solution are ready for use.

The above described various embodiments can be used in this, aspect of the invention.

The solutions and methods of the present invention may be used in conjunction with enzymes to remove debris or deposit material from the contact lens as the solutions of the present invention have no negative effect on the proteolytic activity of enzymes, such as UNIZYME®. After such contacting step, the contact lens optionally may be manually rubbed with saline, or even rinsed without rubbing, to remove further deposit material from the lens. The cleaning method can also include rinsing the lens substantially free of the liquid aqueous medium prior to returning the lens to a wearer's eye.

The previous disclosure will enable one having ordinary, skill in the art to practice the invention. In order to better enable the reader to understand specific embodiments and the advantages thereof, reference to the following examples is suggested.

Example 1

Thionin dye modification and decolorization: A PEG (polyethylene glycol) polymeric tail is attached onto thionin. Experiments are carried out to test whether this modified thionin can stain various contact lenses (Focus® Night and Day™ (FND), Focus® Monthly, Focus® Dailies®, and Cibasoft® lenses, all from CIBA Vision). After 24 hours, there is no apparent uptake into any of the lenses studied. But, the color of the thionin solution is lost. This PEG-thionin is also tested for cytotox testing using a modified USP elution test. It is found that there is no cytotoxicity.

Photobleaching: After about six hours of exposure to a red LED, PEG-thionin is almost completely decomposed (discolorized).

A colored lens care solution containing PEG-thionin is prepared and diluted to the yield the appropriate absorbance range @ 600 nm (0.1-0.15). 6 ml of a sample is exposed to a UV LED with a luminous intensity of 2000 mcd and a viewing angle of 30° for 0, 2, 4 and 6 hrs respectively. It is found that after 4 & 6 hrs color of the solution fades noticeably (i.e., visually distinguishable from the controls). This is also supported by the change in absorbance values, about 39.5%-51.5% reduction in absorbance values.

Example 2

LinaBlue AE Decolorization: It is well known in the literature that LinaBlueAE, a natural product protein from cyanobacteria, is sensitive to light.

A colored lens care solution is prepared from Aquify® MPS (CIBA Vision) by adding LinaBlue AE. The colored solution is subject to 3 cycles in a Purilens cleaning system which contains a UV bulb and a small sonicator to clean lenses. The UV lamp turns on in the system for 15 minute increments. Completely decolorization of the LinaBlue AE Aquify MPS solution can be achieved with 3 cycles. However, when UV, white, and red LEDs are used as light sources to decolorize LinaBlue AE, none of these LEDs succeed to completely decolorize the LinaBlue AE in solution. It believes that the LED exposure is not large enough to decolorize LinaBlue AE within 6 hours. By increasing the number of LEDs in a lens case and/or specially arranging LEDs in a lens case, one may solve this problem. Alternatively, one may rely on singlet oxygen or photocatalysts to decompose a colorant in a colored lens care solution.

Decolorization of Linablue Formulation: A Solocare Aqua solution containing LinablueAE is exposed to UV light using the Purilens system over a couple of 15 min cycles. It is observed that after 3 cycles, the solution is decolorized.

UV Degradation of Linablue Formulations: Two colored lens care solutions containing LinablueAE as the colorant are prepared. Formulation samples both before and after exposure to UV radiation are submitted for cytotoxicity testing using ESP elution test, neutral red uptake/release and AB tests. Results from the tests show no cytotoxicity.

Although various embodiments of the invention have been described using specific terms, devices, and methods, such description is for illustrative purposes only. The words used are words of description rather than of limitation. It is to be understood that changes and variations may be made by those skilled in the art without departing from the spirit or scope of the present invention, which is set forth in the following claims. In addition, it should be understood that aspects of the various embodiments may be interchanged either in whole or in part. Furthermore, titles, headings, or the like are provided to enhance the reader's comprehension of this document, and should not be read as limiting the scope of the present invention. Accordingly, the spirit and scope of the appended claims should not be limited to the description of the preferred versions contained therein.

What is claimed is:

1. A lens care kit for cleaning and disinfecting contact lenses, comprising:
   a colored lens care solution including a water-soluble colorant; and
   a lens case, wherein the lens case comprises a singlet oxygen-generating agent and a light radiation source, wherein the singlet oxygen-generating agent generates singlet oxygen by light irradiation from the light irradiation source, wherein the singlet oxygen decomposes the colorant and renders the colored lens care solution colorless over a specific time period, thereby indicating that lenses under disinfecting and cleaning by the colored lens care solution are ready for use.

2. The lens care kit of claim 1, wherein the colorant is a dye which can be degraded by singlet oxygen within the specific time period.

3. The lens care kit of claim 2, wherein the dye is thionin or thionin modified by attaching a polyethylene glycol polymeric tail thereto.

4. The lens care kit of claim 1, wherein the singlet oxygen-generating agent is covalently attached to the solution-contacting surface of the lens case.

5. The lens care kit of claim 1, wherein the singlet oxygen-generating agent is covalently attached to the surface of a solid support which can be placed in the lens case in contact with the colored lens care solution.

6. The lens care kit of claim 5, wherein the solid support is a glasses, a resin, or a cloth tissue.

7. The lens care kit of claim 5, wherein the solid support has a pinwheel configuration within the confines of the lens case, wherein the pinwheel configuration is covered with a top that allows only a small piece of the pinwheel to be exposed to the lens care solution and light irradiation, wherein the top of the pinwheel is capable of being rotated to allow a fresh amount of singlet oxygen-generating agent to be exposed to the lens care solution and to light irradiation after a number of uses.

8. The lens care kit of claim 1, wherein the colored lens care solution is a multiple purpose solution which is free of hydrogen peroxide.

9. The lens care kit of claim 8, wherein the colored lens care solution comprises a hexamethylene biguanide polymer (PHMB).

10. The lens care kit of claim 9, wherein the hexamethylene biguanide polymer (PHMB) has a molecular weight at least 5 folder larger than that of the colorant.

11. The lens care kit of claim 10, wherein the PHMB is present in an amount of from about 0.01 to about 10 ppm.

12. The lens care kit of claim 1, wherein the colored lens care solution initially has a color of blue or green or purple, and wherein, at the end of the specific time period, the color of the colored lens care solution is substantially disappeared and becomes substantially clear.

13. The lens care kit of claim 1, wherein the colored lens care solution is obtained immediately prior to treating the lens in the lens case by mixing two solutions, one hydrogen peroxide containing solution free of colorant and the other solution containing the colorant and free of hydrogen peroxide.

14. A lens care kit for cleaning and disinfecting contact lenses, comprising:
   a colored lens care solution including a water-soluble colorant; and
   a lens case, wherein the lens case comprises a semiconductor-based photocatalyst, and a light radiation source, wherein the semiconductor-based photocatalyst generates hydroxyl radical and super oxide anion by light irradiation from the light irradiation source, wherein the hydroxyl radical and super oxide anion degrade the colorant and render the colored lens care solution colorless over a specific time period, thereby indicating that lenses under disinfecting and cleaning by the colored lens care solution are ready for use.

15. The lens care kit of claim 14, wherein the photocatalyst is $TiO_2$.

16. The lens care kit of claim 14, wherein $TiO_2$ is applied directly onto the solution-contacting surface of the lens case.

17. The lens care kit of claim 14, wherein $TiO_2$ is applied onto the surface of a solid support which can be placed in the lens case in contact with the colored lens care solution.

18. The lens care kit of claim 17, wherein the solid support is a glasses, a resin, or a cloth tissue.

19. The lens care kit of claim 17, wherein the controlled time period is at least about 2 hour.

* * * * *